United States Patent
McLean et al.

(10) Patent No.: US 6,493,638 B1
(45) Date of Patent: Dec. 10, 2002

(54) SENSOR APPARATUS FOR MEASURING VOLATILE ORGANIC COMPOUNDS

(75) Inventors: Robert A. McLean, Brea; James A. Wurzbach, San Diego, both of CA (US); Harold C. Gilbert, North Kingston, RI (US); Lawrence A. Schatzmann, Yorba Linda, CA (US); Gregory E. Smith, Fullerton, CA (US); Thomas B. Stanford, Port Hueneme, CA (US)

(73) Assignee: Raytheon Company, Lexington, MA (US)

( * ) Notice: Subject to any disclaimer, the term of this patent is extended or adjusted under 35 U.S.C. 154(b) by 0 days.

(21) Appl. No.: 09/516,490

(22) Filed: Mar. 1, 2000

(51) Int. Cl.$^7$ ............................................. G01N 31/00
(52) U.S. Cl. ........................................ 702/22; 702/24
(58) Field of Search ................................ 324/693, 724; 73/31.02; 702/23; 205/787

(56) References Cited

U.S. PATENT DOCUMENTS

| | | | |
|---|---|---|---|
| 5,331,287 A | * 7/1994 | Yamagishi et al. | ......... 324/724 |
| 5,337,018 A | * 8/1994 | Yamagishi | ................... 324/693 |
| 5,417,100 A | * 5/1995 | Miller et al. | ................ 73/31.02 |
| 5,571,401 A | * 11/1996 | Lewis et al. | ................. 205/787 |
| 5,832,411 A | * 11/1998 | Schatzmann et al. | ......... 702/23 |

* cited by examiner

Primary Examiner—Kamini Shah
Assistant Examiner—Douglas N Washburn
(74) Attorney, Agent, or Firm—Colin M. Raufer; Leonard A. Alkov; Glenn H. Lenzen

(57) ABSTRACT

An apparatus for measuring volatile organic compounds in a gas includes a sensor chamber having a housing with a gas inlet, a gas outlet, and a gas flow path from the gas inlet to the gas outlet, a set of baffles within the housing and positioned in the gas flow path, and a set of sensors within the housing and positioned in the gas flow path. Each sensor has an electrically conductive polymer whose electrical properties are dependent upon the presence of specific volatile organic compounds in the gas flow. Desirably, the set of baffles and the set of sensors are cooperatively positioned such that the time for gas to flow from the gas inlet to each of the sensors is substantially the same. The apparatus further includes a pump that removes the gas from the gas outlet of the housing, and an electronic circuit that measures the electrical properties of each of the sensors.

5 Claims, 3 Drawing Sheets

SENSOR APPARATUS FOR MEASURING VOLATILE ORGANIC COMPOUNDS

This invention was made with Government support under Contract No. N00014-95-2-0008 awarded by the Department of the Navy. The Government has certain rights in this invention.

BACKGROUND OF THE INVENTION

This invention relates to the monitoring of gases to detect levels of volatile organic compounds, and, more particularly, to a sensor apparatus useful in such monitoring.

Volatile organic compounds (VOCs) are associated with many industrial processes. VOCs such as solvents (e.g., benzene, toluene, xylene, ketones, acetates, alcohols) are typically used in the processes in liquid form, but may evaporate into the process environment. Some of the VOCs are health hazards and/or contribute to the formation of atmospheric pollutants.

In one example, industrial painting operations utilize large amounts of VOC solvents as carriers for pigments. The solvents evaporate to some degree during the painting as a result of the use of mildly elevated temperatures and/or the use of techniques such as spray painting which utilize finely divided droplets containing the solvents. Great care is taken to confine the solvents to closed systems, but inevitably there is some leakage at joints in the apparatus, input/output ports, and other locations.

Measuring the presence and concentrations of VOCs is of importance in several ways. For example, regulators compare the concentrations of VOCs to regulatory standards to ensure compliance of industrial operations to the standards, and to determine whether certain operations may be allowed to continue. Process engineers use information on VOC production to select processes for implementation. VOC information is used to determine whether a process is operating properly, and to identify sources of inefficient operation. Medical personnel seek to correlate human health with VOC concentrations.

The VOCs are typically present in the range of parts per billion or parts per million of the process gas such as air. Instruments are available to make quantitative measurements of the gas for VOCs at such low levels. Examples of such instruments include flame ionization detectors, Fourier transform infrared spectrometers, and instruments using other wet or dry chemical analysis procedures. Such instruments tend to be relatively expensive and bulky, and require trained personnel to operate them. It is therefore not ordinarily possible to place the measurement instruments at all locations where information might be needed, such as at a plurality of different sampling locations around a paint line. Instead, individual gas samples may be transported, or samples may be piped, from the sampling locations to the central measurement instrument. These approaches are accompanied by concerns that the composition of the sample may change during transport, or that the sampling loses its real-time character. The latter is of particular concern for process engineers who use the sampling data to optimize the operation and performance of the industrial system.

There is a need for an improved practical approach to the sampling and measurement of VOCs in industrial and other environments. The present invention fulfills this need, and further provides related advantages.

SUMMARY OF THE INVENTION

The present invention provides an apparatus for measuring volatile organic compounds (VOCs) in a real-time manner with excellent sensitivity. The apparatus is relatively inexpensive, so that units may be placed at various locations around an industrial operation to assess production of VOCs in the industrial operation. The apparatus is suitable for measuring a wide variety of VOCs using the same basic structure, modified only as to the sensor selected for each particular VOC. A single instrument may analyze for a number of VOCs simultaneously.

In accordance with the invention, the apparatus for measuring volatile organic compounds in a gas comprises a sensor chamber, which includes a housing having a gas inlet, a gas outlet, and a gas flow path from the gas inlet to the gas outlet, a gas flow path control structure within the housing to alter the gas flow from the gas inlet to the gas outlet, and a set of sensors within the housing and positioned in the gas flow path. Each sensor has an associated sensor electrical output signal that is dependent upon the presence of a respective volatile organic compound in the gas flow. The apparatus optionally includes a pump that removes the gas from the gas outlet of the housing, and an electronic circuit that measures each of the sensor electrical output signals.

The gas flow path control structure is preferably a set of baffles that spread the gas flow through a volume and to the set of sensors. Desirably, the gas flow path control structure and the set of sensors are cooperatively positioned so that the time required for the gas to flow from the gas inlet to each of the sensors is substantially the same. The apparatus may also be provided with appropriate sensors of its conditions, such as temperature and humidity sensors. The conditions of the apparatus, such as its temperature, may be controlled, as with a heating element to control the temperature in a closed-loop fashion. A microcontroller controls and coordinates operation of the apparatus, including the electronics, pump (where present), sensors, heating elements, and the like.

The sensors preferably include electrically conductive polymers whose electrical properties depend upon the presence of the respective volatile organic compounds in the gas flow contacting the polymer. Various polymers whose electrical properties are sensitive to organic compounds, such as methyl isoamyl ketone, xylene, and butyl acetate, are known.

The present approach provides a compact apparatus for measuring VOCs. The apparatus is relatively compact and light, permitting it to be positioned at locations where measurements are required, or for a number of the apparatus units to be positioned at a number of locations where measurements are required. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
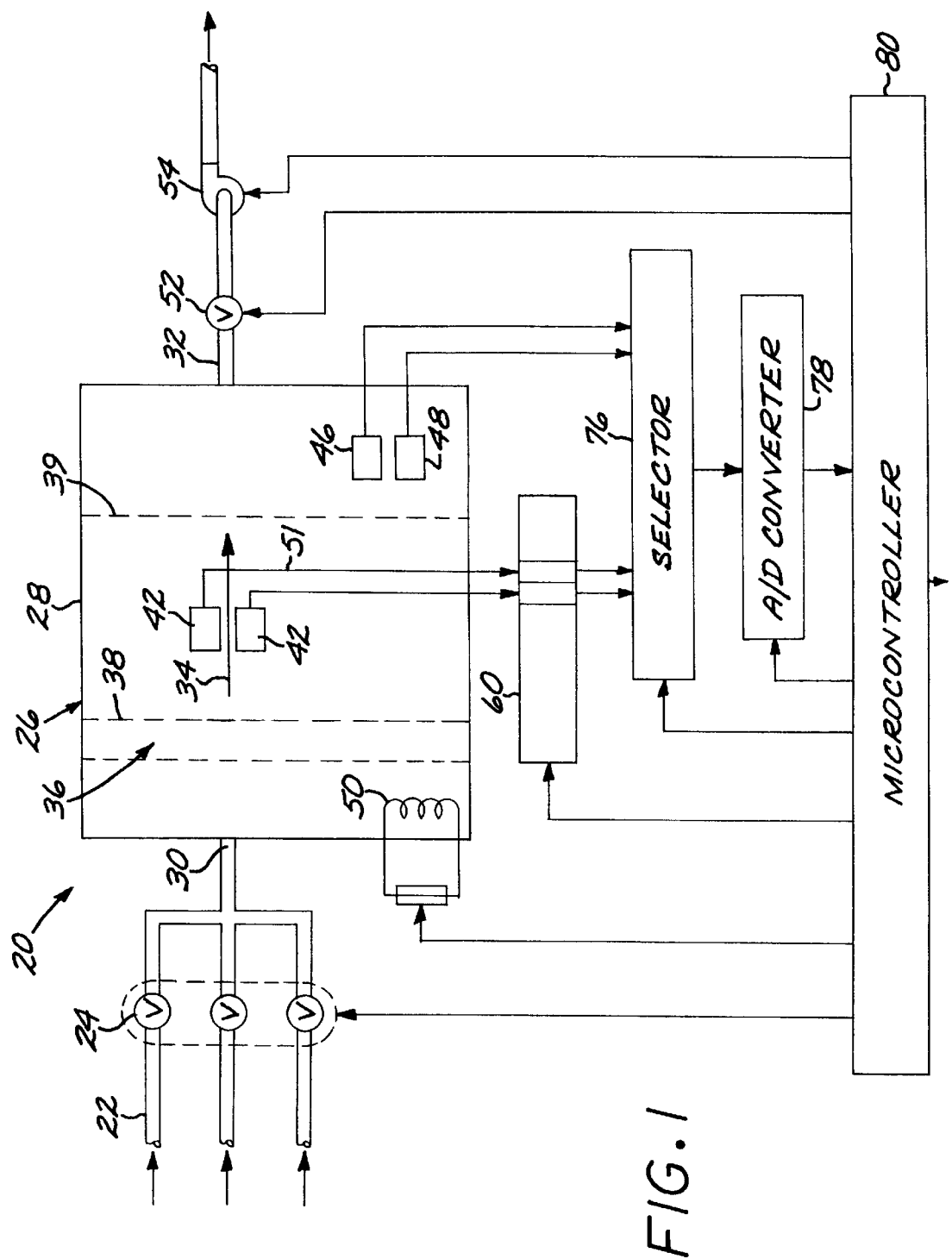
FIG. 1 is a schematic diagram of the apparatus of the invention.

FIG. 1 illustrates an apparatus 20 according to the invention. The apparatus may be used in a stand-alone fashion, or it may serve as one of the sensor units of a network of sensor units such as that disclosed in U.S. Pat. No. 5,832,411. The apparatus 20 receives gas flows that potentially contain volatile organic compounds through input lines 22, here illustrated as three input lines 22 that are accessed through respective input valves 24. At least one of the input lines 22 is connected to a source of a gas which is to be measured for the presence and/or the concentration of volatile organic compounds therein. One or more of the input lines 22 may be connected to a source of a standard reference gas having a known concentration of a particular volatile organic compound, for the purpose of calibrating the sensors of the apparatus 20. A selected one of the gas flows from the input lines 22 is delivered to a sensor chamber 26. The sensor chamber 26 has a housing 28 with a gas inlet 30, a gas outlet 32, and a gas flow path 34 from the gas inlet 30 to the gas outlet 32.

A gas flow control structure 36 is contained within the housing 28. The gas flow control structure 36 distributes the gas flow in the gas flow path 34 in a generally uniform manner throughout the cross-sectional area of the gas flow path 34. Any operable gas flow control structure 36 may be used. In the preferred case, the gas flow control structure 36 includes a set of baffles 38, which are illustrated schematically in FIG. 1 and shown in greater detail in FIGS. 2 and 3. The baffles 38 are arranged to create a turbulent flow to redistribute the gas flow entering the housing 28 through the gas inlet 30, into a series of flows that are generally evenly and uniformly distributed across a width 40 of the housing 28.

A set of sensors 42 are positioned within the housing 28. The sensors 42 are preferably distributed laterally across the width 40 of the housing 28 and in the gas flow path 34. In the illustrated embodiment of FIG. 2, there are eight sensors 42, but there may be more or fewer sensors. The sensors 42 are positioned equidistantly downstream of a corresponding number of openings 44 in the last of the baffles 38 interposed in the gas flow path 34.

The gas flow control structure 36 also includes a similar baffle arrangement 39 downstream of the sensors 42 and before the gas outlet 32, to equalize the flow path 34 for the exhaust gas.

Figure 2:
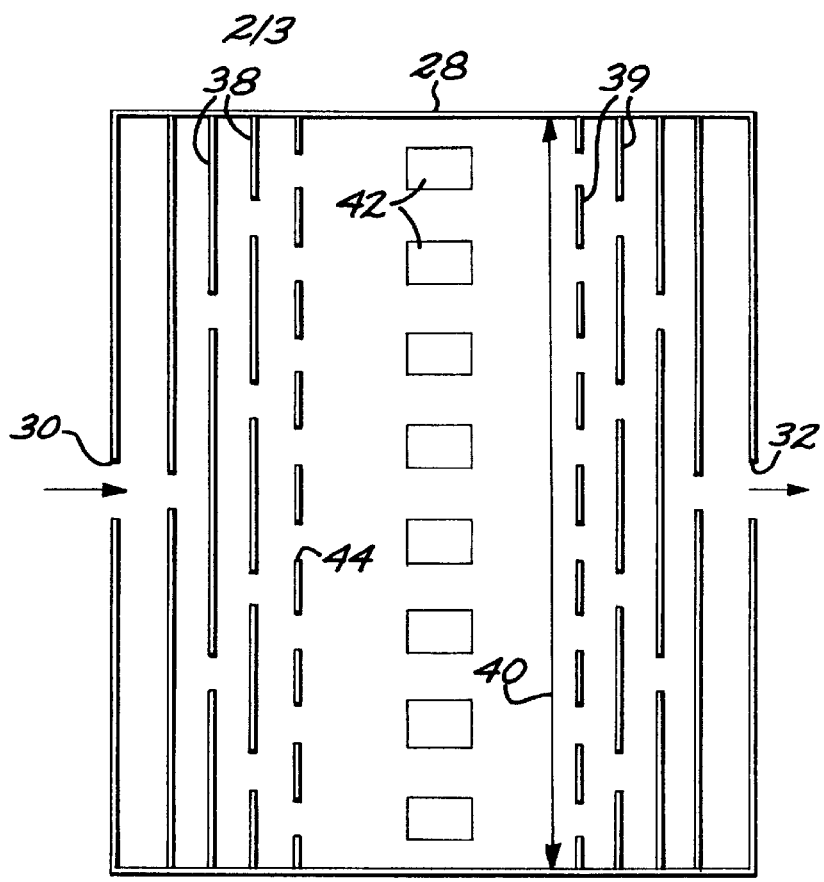
FIG. 2 is a detail interior plan view of the sensor chamber.
Figure 3:
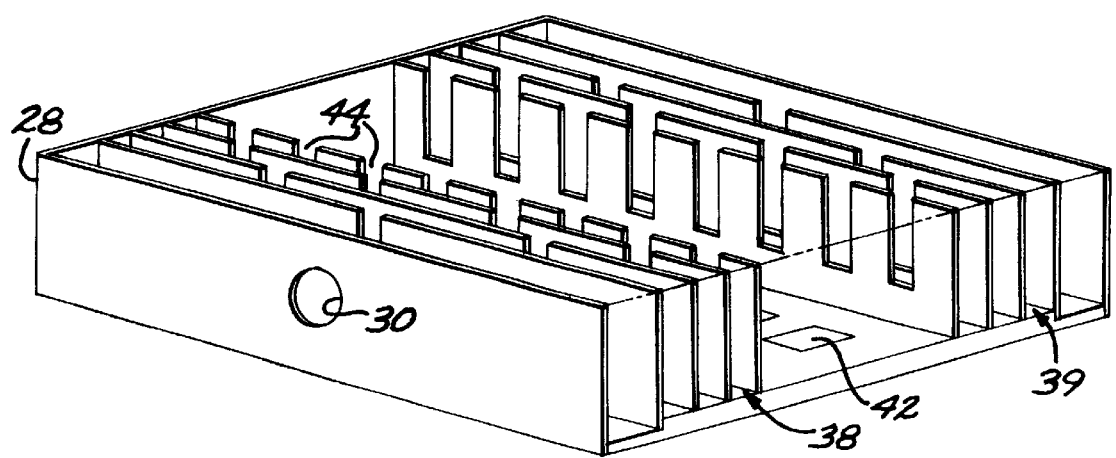
FIG. 3 is a perspective view of the sensor chamber, with the front side and top housings removed to illustrate the interior arrangement.

In the arrangement preferred for use with real-time measurements, the baffles 38 and 39 and the sensors 42 are cooperatively positioned, as shown in FIGS. 2 and 3, such that the time for gas to flow from the gas inlet 30 to each of the sensors 42 is substantially the same. This arrangement is desirable for apparatus 20 to be used in real-time measurements of volatile organic compounds in flowing gas samples, because the outputs of each of the sensors correspond to the same time sampling of the gas. Such real-time measurements from the same time sampling are particularly useful in the analysis of operating procedures in production settings, such as the determination of the proper operating conditions of a paint line. The real-time gas samples allow accurate determinations of the effects of changing operating parameters on the performance of the system as a function of time.

The sensor chamber 26 may also be provided with environmental sensors (different from the sensors 42) to measure the environment within the housing 28. Such environmental sensors may include, for example, a temperature sensor 46 and/or a humidity sensor 48. To control the temperature within the sensor chamber 26, a heating element 50 such as an electrical resistance heater may optionally be provided on or within the housing 28.

The set of sensors 42 measure the presence and/or the concentration of various types of volatile organic compounds (VOCs) in the gas flow introduced through the gas inlet 30. The sensors 42 preferably comprise electrically conductive polymers whose electrical resistivity depends on the presence and/or the concentration of respective volatile organic compounds in the gas flow. Such electrically conductive polymers are known in the art and are disclosed, for example, in U.S. Pat. Nos. 5,337,018; 5,331,287; and 5,417,100. The sensors 42 are generally fabricated with different conductive polymer formulations that produce varying responses when exposed to the gas flow containing the VOCs. Typically, all of the different sensors 42 respond to each of the VOCs, with different responses for each of the sensors 42 to each VOC. Collectively, the distribution of responses is characteristic of the gas flow and constitutes a signature that is used to classify, speciate, and quantify each VOC. A number of such individual sensors 42 are therefore included in the sensor chamber 26. In the example of FIG. 1, there are two sensors 42. In the example of FIG. 2, there are eight sensors 42. Fewer or more sensors 42 may be provided, according to the specific measuring requirements for a system. The physical structure of the sensor chamber 26 and the electronics to be described subsequently are readily capable of accommodating a wide range in the numbers and types of the sensors 42. Each of the sensors 42 has a sensor electrical output signal 51.

Gas leaves the sensor chamber 26 through the gas outlet 32. It passes through an exit valve 52 and a pump 54. The pump 54 functions to draw the gas flow through the sensor chamber 26. The pump 54 may be a box fan, a centrifugal blower, rotary vane pump, or any other operable type. The pump 54 need not be of large capacity, since the gas flow rate through the sensor chamber 26 is relatively low.

The present approach may also be used without a pump. Where there is no pump, the apparatus depends upon diffusion of gas to the sensors 42, a condition which may be achieved in some situations. Because the pump is one of the major consumers of electrical power in the apparatus, omitting the pump substantially reduces the power requirements of the apparatus so that it is more suited for battery-powered operation in remote locations.

The gas exiting the apparatus 20 is disposed of, either by venting or cleaning to remove the VOCs.

The apparatus 20 further includes an electronic circuit 60 that measures the electrical output signal 51 of each sensor 42. In the preferred polymer-based sensor 42 described earlier, the electrical resistivity of the polymer varies according to the presence and/or the concentration of the respective volatile organic compound in the gas flow to which the polymer and sensor 42 are sensitive. The electronic circuit 60 measures that change in resistivity, and any operable circuitry to accomplish that measurement of the resistance change may be used. An electronic circuit 60 may be constructed that is sufficiently inexpensive that an individual circuit may be provided for each of the sensors 42, as shown in FIG. 1. Equivalently for the present purposes, the output signals 51 of all of the sensors 42 may be multiplexed to a single electronic circuit 60.

Figure 4:
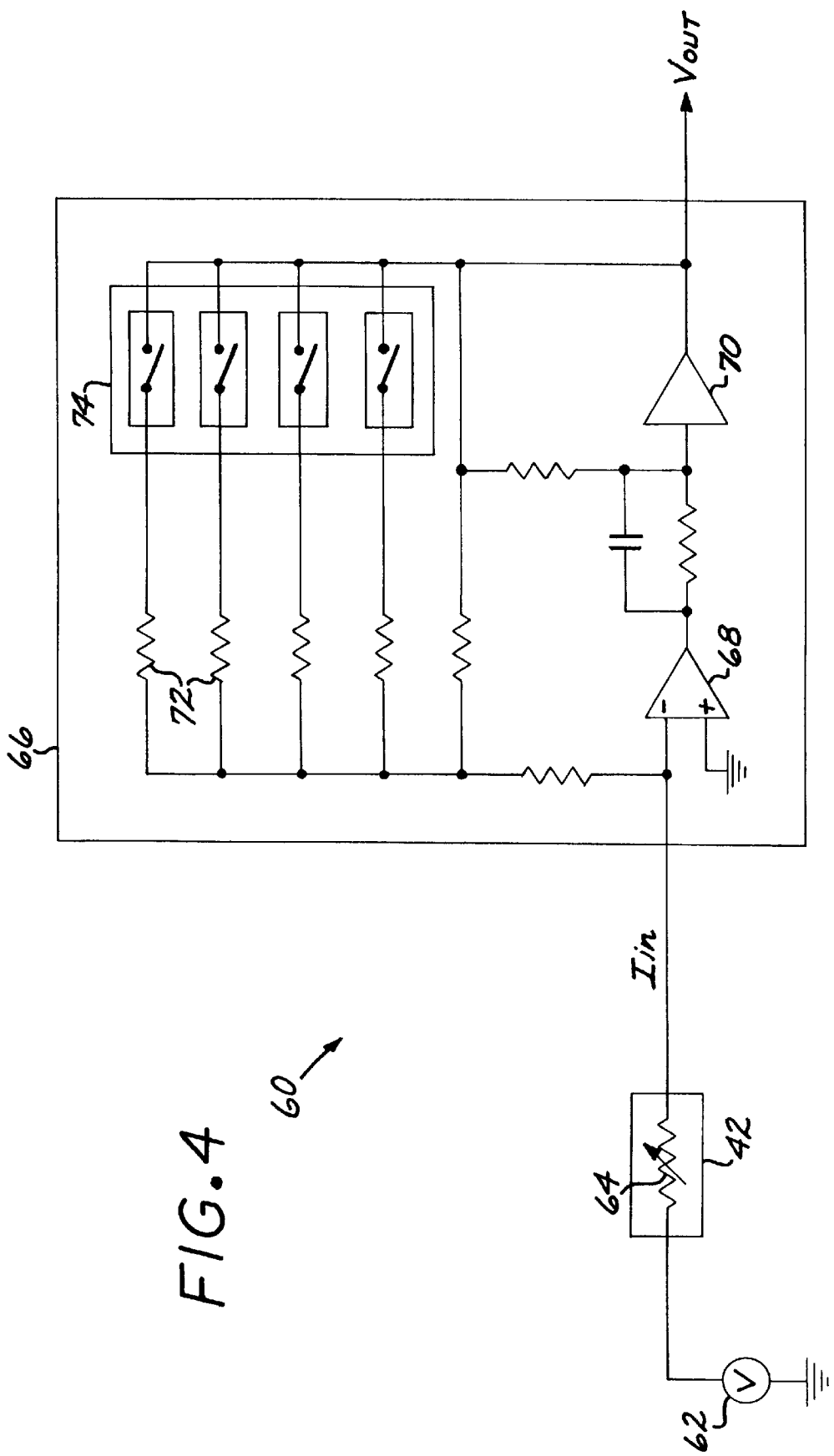
FIG. 4 is a circuit diagram of a preferred sensor electronics.

FIG. 4 illustrates a preferred such electronic circuit 60 for measuring the electrical properties of the sensor 42, and in this case providing a signal related to the electrical resistivity of its polymer component whose resistivity varies according to the presence and/or the concentration of a particular volatile organic compound. A voltage signal 62 is applied to the polymer component 64, indicated schematically as a variable resistor. The voltage signal 62 may be a constant DC voltage or a periodic voltage. Preferably, the voltage signal 62 is a +/−10 millivolt square wave with a frequency of 1 kilohertz. The current through the polymer component 64, $I_{in}$, is provided to a current-to-voltage conversion circuit 66. $I_{in}$ is fed to the negative input of an operational amplifier 68, whose positive input is referenced to ground. The output of the operational amplifier 68 is supplied to a voltage follower 70. The output of the voltage follower 70 is supplied to one or more of a set of feedback resistors 72 of different fixed resistances whose connection into the circuit is controlled by a CMOS switch set 74. The appropriate resistors are selected to accommodate the range of currents to be measured through the polymer component 64. The output of this circuit 66 is a voltage $V_{out}$ related to the resistance of the polymer component 64.

Returning to the discussion of FIG. 1, the voltage outputs of the electronic circuit 60, and of the environmental sensors such as sensors 46 and 48, are supplied to a selector 76, which functions as a switch to select one of the sensors at a time to be monitored. The selected output, still in analog form, is provided to an analog-to-digital converter 78. The digital output is provided to a microcontroller 80.

The microcontroller 80 receives sensor information, both for the VOC sensors 42 and for the environmental sensors such as sensors 46 and 48, through the analog-to-digital converter 78. It also provides command outputs to coordinate the operation of the valves 24 and 52, the heating element 50, the electronic components 60, 76, and 78, the pump 54 (where present), and any other optional controllable elements of the apparatus 20. The microcontroller 80 furthermore formats and communicates the measured sensor data to an external computing equipment for analysis and display.

A breadboard apparatus 20 has been constructed and tested. The breadboard apparatus 20 has a size of 20 inches by 20 inches by 8 inches and weighs about 50 pounds in an industrial enclosure. It has proved fully operational as discussed, for measuring a VOC challenge vapor consisting of methyl isoamyl ketone (MIAK), xylene, and butyl acetate (BuOAc), which are solvents commonly used for paint booth operations. The apparatus 20 has consistently demonstrated a sensitivity for individual VOCs down to the 1 part-per-million (ppm) level, with indications that sensitivities of 0.1 ppm and below may be possible for certain lower vapor pressure compounds. The measurements are made in real time, at a rate of 1000 samples per second. The temperature sensor 46 and the heating element 50 regulated the temperature of the sample gas flow to within +/−0.05 degrees Celsius.

A compact version of the apparatus 20 has been designed but not constructed. The compact version is estimated to have a size of 15 inches by 11 inches by 7 inches and a weight of 15 pounds. Preliminary studies have shows that further reduction in volume may be accomplished for a production apparatus 20 through repackaging of the sensor chamber 26 and the electronic circuit 60. The apparatus is therefore suitable for placement at a wide variation of locations, and several may be used in conjunction with a large-scale commercial fabrication operation.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for measuring volatile organic compounds in a flowing gas sample, comprising:

a source of a flowing gas sample;

a sensor chamber, comprising
   a housing having a gas inlet from the source of the flowing gas sample, a gas outlet, and a gas flow path from the gas inlet to the gas outlet,
   a set of baffles within the housing and positioned in the gas flow path from the gas inlet to the gas outlet, and
   a set of sensors within the housing and positioned in the gas flow path, each sensor having an associated sensor electrical output signal that is dependent upon the presence of specific volatile organic compounds in the gas flow, wherein the set of baffles and the set of sensors are cooperatively positioned such that the time for gas to flow from the gas inlet to each of the sensors is substantially the same; and an electronic circuit that measures each of the sensor electrical output signals.

2. The apparatus of claim 1, wherein the apparatus further includes a heating element that heats at least a portion of the sensor chamber.

3. The apparatus of claim 1, wherein at least some of the sensors include an electrically conductive polymer whose electrical conductivity depends upon the presence of specific volatile organic compounds in the gas flow.

4. The apparatus of claim 1, further including a programmed microcontroller operable to control the apparatus.

5. The apparatus of claim 1, further including a pump that forces a flow of the gas through the sensor chamber.

* * * * *